(12) United States Patent
Freeman

(10) Patent No.: US 9,655,809 B2
(45) Date of Patent: *May 23, 2017

(54) METHOD AND DEVICE FOR PERFORMING ALTERNATING CHEST COMPRESSION AND DECOMPRESSION

(71) Applicant: ZOLL Medical Corporation, Chelmsford, MA (US)

(72) Inventor: Gary Freeman, Chelmsford, MA (US)

(73) Assignee: ZOLL Medical Corporation, Chelmsford, MA (US)

(*) Notice: Subject to any disclaimer, the term of this patent is extended or adjusted under 35 U.S.C. 154(b) by 46 days.

This patent is subject to a terminal disclaimer.

(21) Appl. No.: 14/576,029

(22) Filed: Dec. 18, 2014

(65) Prior Publication Data

US 2015/0105705 A1    Apr. 16, 2015

Related U.S. Application Data

(63) Continuation of application No. 13/631,289, filed on Sep. 28, 2012, now Pat. No. 8,920,348.

(51) Int. Cl.
*A61H 31/00* (2006.01)
*A61N 1/39* (2006.01)

(52) U.S. Cl.
CPC ..... *A61H 31/006* (2013.01); *A61H 2031/001* (2013.01); *A61H 2201/013* (2013.01);
(Continued)

(58) Field of Classification Search
CPC ............ A61H 31/006; A61H 2031/001; A61H 2201/1664; A61H 2201/013;
(Continued)

(56) References Cited

U.S. PATENT DOCUMENTS 2,255,684 A * 9/1941 Smith ................... A61H 9/005
601/10
2,910,264 A * 10/1959 Lindenberger .......... F16B 47/00
248/206.2
(Continued)

FOREIGN PATENT DOCUMENTS

CN    2209523 Y    10/1995
CN    2250157 Y    3/1997
(Continued)

OTHER PUBLICATIONS

Extended European Search Report dated Mar. 23, 2016 from European Patent Application No. 13840819.0.

*Primary Examiner* — Justine Yu
*Assistant Examiner* — Timothy Stanis
(74) *Attorney, Agent, or Firm* — ZOLL Medical Corporation

(57) ABSTRACT

A plunger adapter and a detachable compression pad for piston driven chest compression devices optimizes the application of chest compressions to a fixed location on a patient's chest. The detachable compression pad may be removably secured to the patient above the patient's sternum to ensure that the compression pressure from the piston through the piston adapter is applied to a fixed location on the patient's chest. As the plunger and plunger adapter retract from the chest, the compression pad remains fixed to the patient's chest, and as the plunger and plunger adapter extend from the chest compression unit for subsequent compression strokes, the distal end of the plunger adapter reengages the compression pad to apply compression to a fixed location on the patient's chest.

12 Claims, 7 Drawing Sheets

(52) U.S. Cl.
CPC ............... *A61H 2201/123* (2013.01); *A61H 2201/1215* (2013.01); *A61H 2201/1664* (2013.01); *A61H 2230/04* (2013.01); *A61N 1/3968* (2013.01)

(58) Field of Classification Search
CPC ...... A61H 2201/1215; A61H 2201/123; A61H 2230/04
See application file for complete search history.

(56) References Cited

U.S. PATENT DOCUMENTS

| | | | | |
|---|---|---|---|---|
| 3,514,065 A | * | 5/1970 | Donaldson | F16B 47/00 248/206.2 |
| 5,318,262 A | * | 6/1994 | Adams | F16B 47/00 248/205.8 |
| 5,327,887 A | | 7/1994 | Nowakowski | |
| 5,582,580 A | * | 12/1996 | Buckman, Jr. | A61M 1/1068 601/107 |
| 5,645,522 A | * | 7/1997 | Lurie | A61H 31/00 601/43 |
| 8,702,633 B2 | | 4/2014 | Voss et al. | |
| 2004/0116840 A1 | | 6/2004 | Cantrell et al. | |
| 2005/0054958 A1 | | 3/2005 | Hoffmann | |
| 2008/0119766 A1 | | 5/2008 | Havardsholm et al. | |
| 2010/0185127 A1 | * | 7/2010 | Nilsson | A61H 31/004 601/41 |
| 2011/0201979 A1 | * | 8/2011 | Voss | A61H 31/005 601/41 |
| 2012/0238922 A1 | | 9/2012 | Stemple et al. | |

FOREIGN PATENT DOCUMENTS

| | | |
|---|---|---|
| CN | 101579286 A | 11/2009 |
| CN | 102028611 A | 4/2011 |
| WO | WO2011155604 A1 | 12/2011 |

* cited by examiner

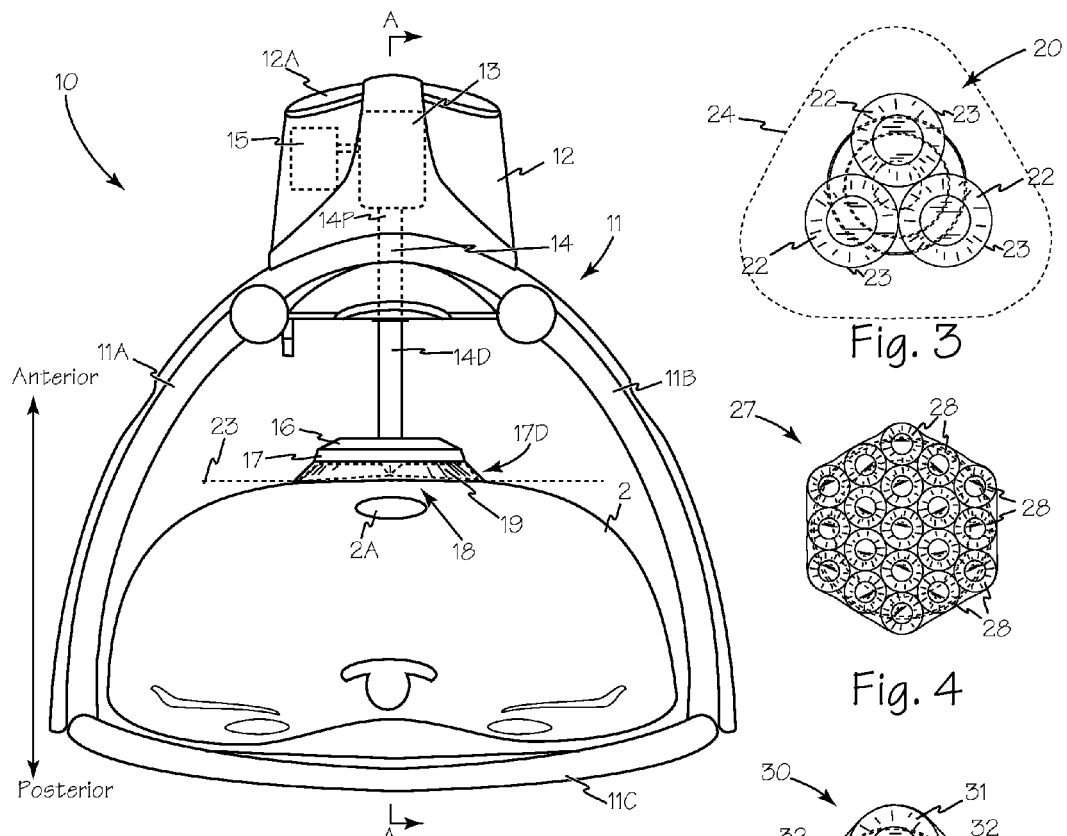

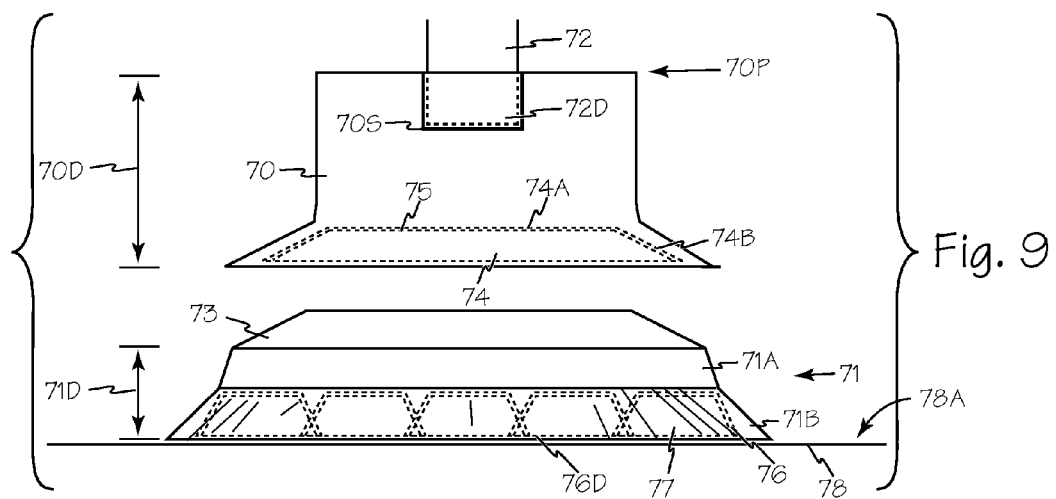
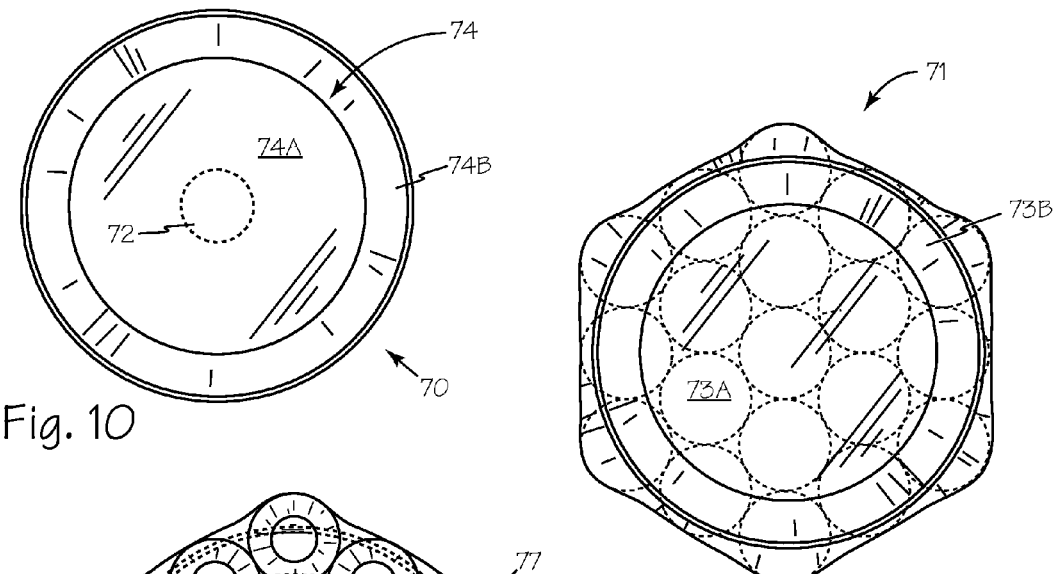
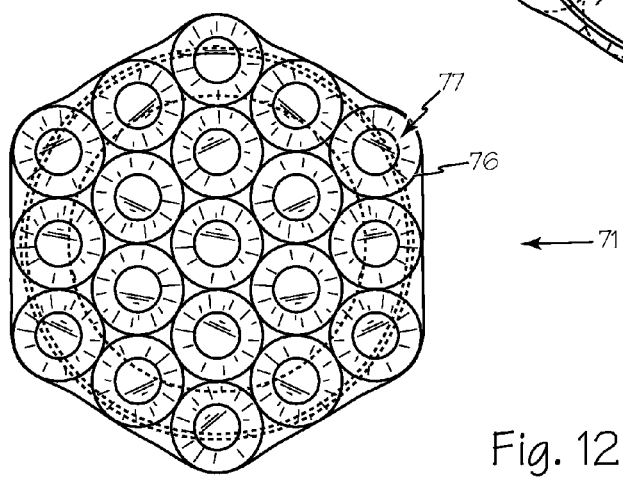

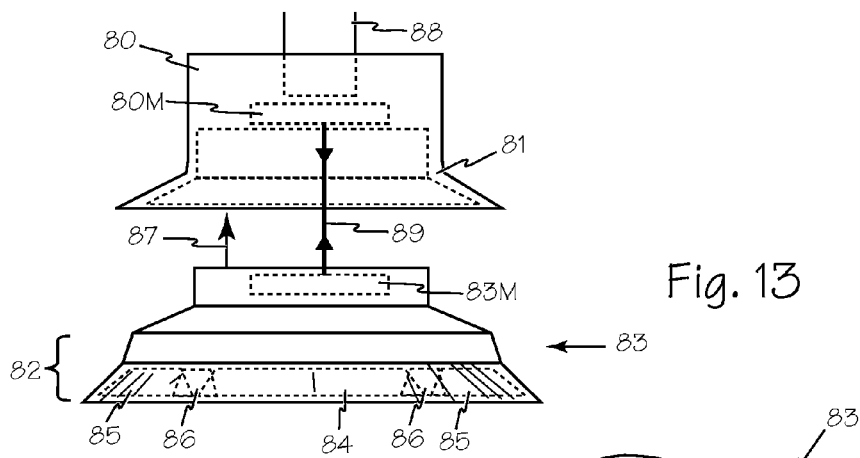
Fig. 13
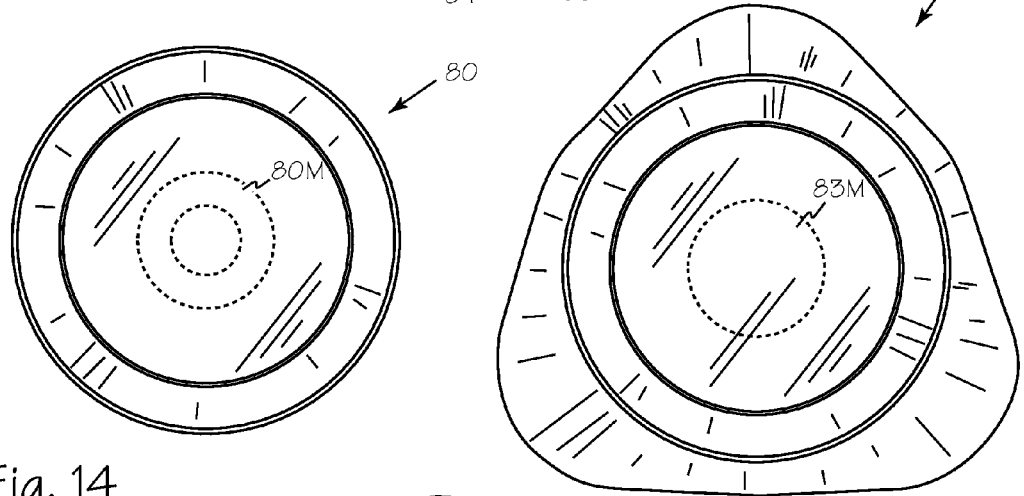
Fig. 14
Fig. 15
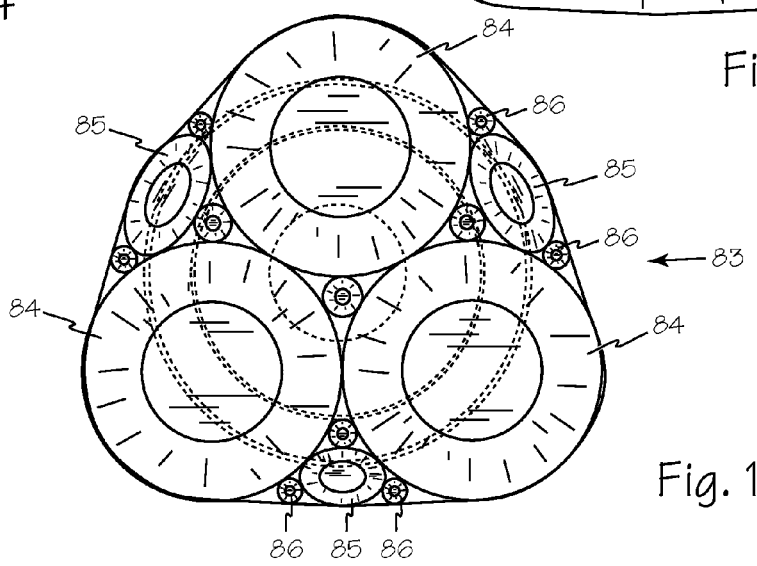
Fig. 16

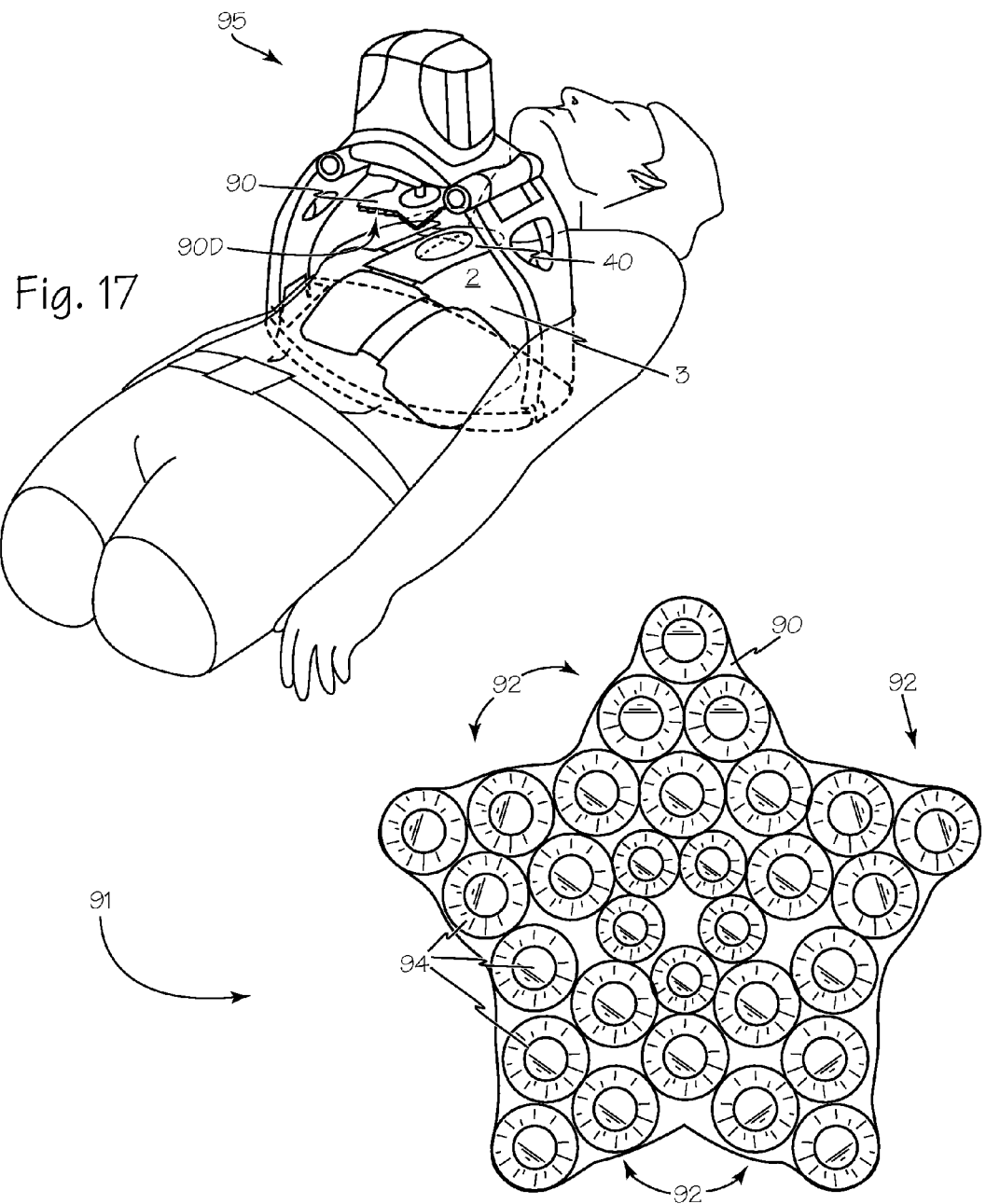

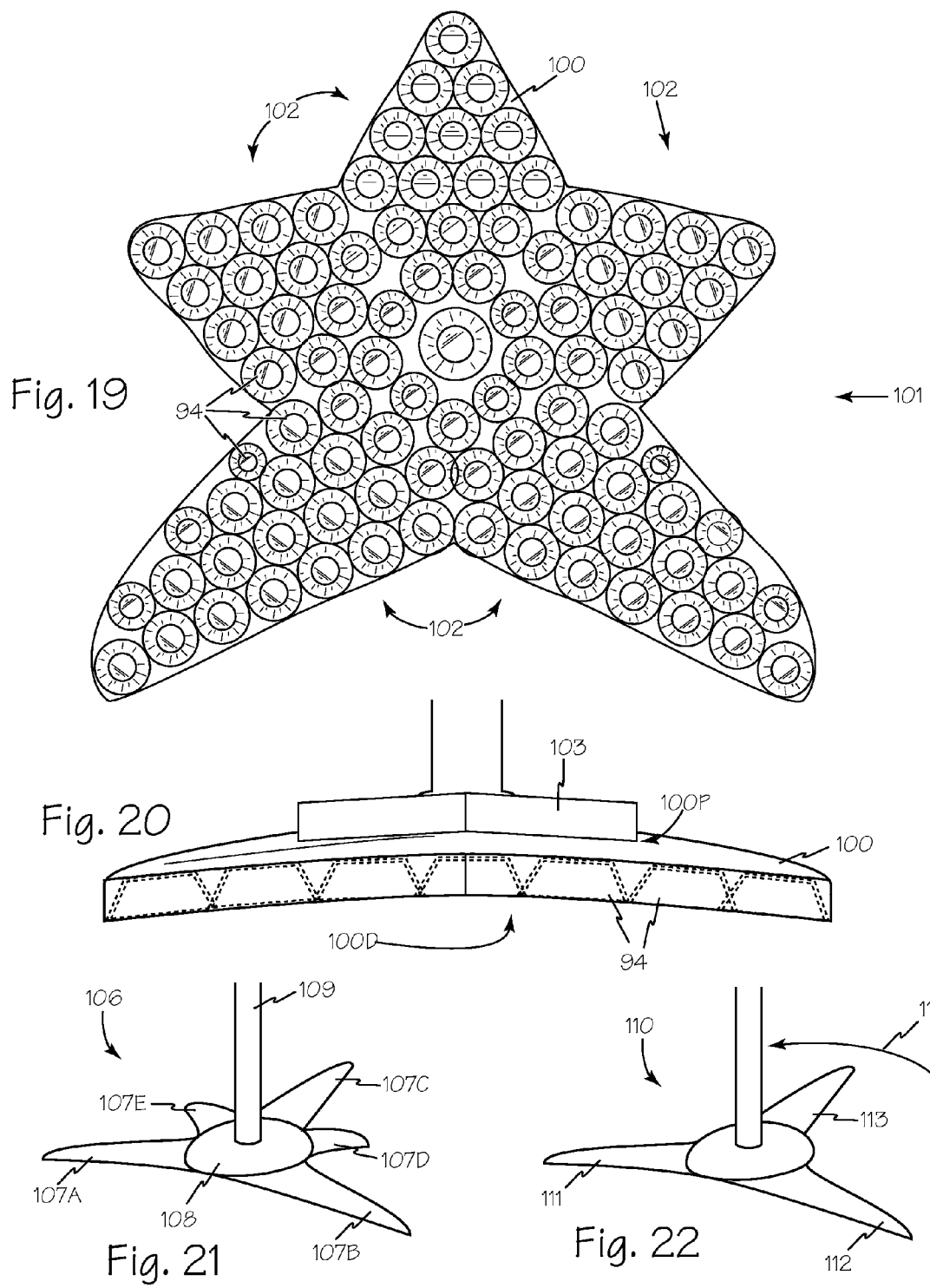

METHOD AND DEVICE FOR PERFORMING ALTERNATING CHEST COMPRESSION AND DECOMPRESSION

This application is a continuation of U.S. patent application Ser. No. 13/631,289 filed Sep. 28, 2012, now U.S. Pat. No. 8,920,348.

FIELD OF THE INVENTIONS

The inventions described below relate the field of cardiopulmonary resuscitation (CPR).

BACKGROUND OF THE INVENTIONS

According to the American Heart Association nearly 383,000 out-of-hospital sudden cardiac arrests occur annually in the United States. These patients may be saved by the timely application of life saving measures such as Cardiopulmonary resuscitation (CPR).

CPR is a well-known and valuable method of first aid used to resuscitate people who have suffered from cardiac arrest. CPR requires repetitive chest compressions to squeeze the heart and the thoracic cavity to pump blood through the body. Artificial respiration, such as mouth-to-mouth breathing or a bag mask device, is used to supply air to the lungs. When a first aid provider performs manual chest compression effectively, blood flow in the body is about 25% to 30% of normal blood flow. However, even experienced paramedics cannot maintain adequate chest compressions for more than a few minutes. Hightower, et al., *Decay In Quality Of Chest Compressions Over Time*, 26 Ann. Emerg. Med. 300 (September 1995). Thus, CPR is not often successful at sustaining or reviving the patient. Nevertheless, if chest compressions could be adequately maintained, then cardiac arrest victims could be sustained for extended periods of time. Occasional reports of extended chest compression efforts (45 to 90 minutes) have been reported, with the victims eventually being saved by coronary bypass surgery. See Tovar, et al., *Successful Myocardial Revascularization and Neurologic Recovery*, 22 Texas Heart J. 271 (1995).

In efforts to provide better blood flow and increase the effectiveness of bystander resuscitation efforts, various mechanical devices have been proposed for performing AUTOMATED CHEST COMPRESSIONS. There are currently two types of automated chest compression devices. One type uses a belt placed around the patient's chest to effect chest compressions. The AutoPulse® chest compression is one such device, and is described in patents such as Mollenauer, et al., *Resuscitation Device having a Motor Driven Belt to Constrict/Compress the Chest*, U.S. Pat. No. 6,142,962 (Nov. 7, 2000). The other type uses a piston which repeatedly compresses the chest. Piston based chest compression systems include the LUCAS® chest compression device (illustrated in Sebelius, et al., *Rigid Support Structure on Two Legs for CPR*, U.S. Pat. No. 7,569,021 (Aug. 4, 2009)) and the THUMPER® chest compression device (illustrated in Barkolow, Cardiopulmonary Resuscitator Massager Pad, U.S. Pat. No. 4,570,615 (Feb. 18, 1986). These chest compression systems include a piston and a motor for repeatedly driving the piston downwardly on the chest, and lifting the piston from the chest to allow the chest to expand under its own natural resistance. Some have proposed improving piston-based CPR with a technique called active compression/decompression, which involves actively lifting the chest wall between CPR compressions. Sebelius, et al., *Positioning Device For Use In Device For Treating Sudden Cardiac Arrest*, U.S. Pat. No. 7,841,996 (Nov. 30, 2010) proposes use of a suction cup on the bottom of the piston, to secure the chest of the patient to the piston. In this manner, the piston, upon upward movement, actively lifts the patient's chest, or at least exerts some upward force on the anterior wall of the chest, to speed the expansive of the chest between each compression. A manual CPR assistance device, the RESQPUMP®, (Advanced Circulatory Systems), also includes a suction cup on the bottom of a manually operated compression pad. This is also proposed to provide lifting force, through the suction cup, on the anterior surface of the chest during the upstroke of the compression cycle.

SUMMARY

The devices and methods described below provide for improved attachment of a compression pad of a piston-based chest compression device to a patients chest, to provided improved active compression/decompression CPR. The device includes a compression pad for piston driven chest compression devices that enables and optimizes compression and decompression force. The compression pad includes two or more suction cups, vacuum cups or suckers to engage the surface of the patient's chest and provide improved decompression force to the patient's chest during mechanical CPR.

When the rim or distal edges of the suction cups are pressed against the surface of the patient's chest and the proximal ends of the suction cups are pressed during chest compression, the volume of the space within the suction cup and the chest surface is reduced, which causes the fluid, air, between the cup and the chest to be expelled past the rims of the suction cups. When the chest compression device ends its compression stroke and is pulled upward in the decompression stroke, suction created between the suction cups and the chest helps secure the compression pad to the chest. As the material of the compression pad tends to resume its original shape when lifted, and some air has already been forced out of the space inside of the cups, the pressure in each of the suction cup spaces is lower that atmospheric pressure which enables the compression pad to exert some decompression force on the patient's chest. The pressure difference between the atmosphere on the outside of the cup is what keeps the cup adhered to the surface and enables decompression force to be exerted on the patient's chest.

The upward force developed by a suction cup is a function of the area of the suction cup. Using multiple suction cups on a compression pad enables the pressure of each suction cup to be kept low while the combined decompression force of all the suction cups of a compression pad is high enough to provide meaningful chest decompression. Balancing the suction force of multiple small suction cups against the total force for all the suction cups on a compression pad eliminates injury to a patient's chest that may occur with a single large suction cup. The suction cups may adopt any useful shape to optimize the number of suction cups on a compression pad and to optimize the decompression force on a patient's chest as well as optimizing the application of compression force to the patient's chest. Also, the use of numerous, small suction cups facilitates conformance of the suction cups to complex 3-D shapes such as the surface of the patient's chest. Improved surface conformance results in improved sealing of the suction cups to the patient's skin, further enhancing the amount of upward force that can be applied by the device. Multiple suction cups on the distal side of the compression pad enables the decompression force applied by the retraction of the plunger adapter to be limited to prevent dissecting injury to the tissues of a patient's chest.

A compression orientation pad may be secured to the patient's chest to provide a readily visible landmark for applying the chest compression, to provide a smooth surface for achieving suction to enable decompression force to be applied, and to incorporate ECG and defibrillation electrodes and other suitable rescue components. Alternatively, any smooth sticker or adhesive sheet may be used as a landmark and to provide a smooth surface for optimizing the suction of the compression pad against the patient's chest.

To provide a controllable mechanism for applying upward force on the patient's chest, a detachable plunger adapter and a cooperating compression pad adhered via suction to the patient's chest may be used. Detachment mechanisms between the plunger adapter and the compression pad which can be readily limited in the amount of upward force which might be applied include magnetic or frictional attachment between the compression pad and the adapter. The attachment force between the plunger adapter and the compression pad can thus be predetermined and limited.

BRIEF DESCRIPTION OF THE DRAWINGS

FIG. 1 is a front view of a piston driven chest compression device with a suction compression pad and a cross section of a patient's chest showing landmark skeletal structures.

FIG. 2 is a cross section of the chest compression device of FIG. 1 taken along A-A with a separable plunger adapter and compression pad.

FIG. 3 is an end view of the distal end of the compression pad of FIG. 1.

FIG. 4 is an end view of the distal end of an alternate compression pad for the device of FIG. 1.

FIG. 5 is an end view of the distal end of another alternate compression pad for the device of FIG. 1.

FIG. 9 is a side view of a plunger adapter and compression pad.

FIG. 10 is an end view of the distal end of a plunger adapter with a frusto-conical socket.

FIG. 11 is an end view of the proximal end of a compression pad with an extension corresponding to the frusto-conical socket of the plunger adapter of FIG. 9.

FIG. 12 is an end view of the distal end of the compression pad of FIG. 9.

FIG. 13 is a side view of an alternate plunger adapter and compression pad.

FIG. 14 is an end view of the distal end of the plunger adapter of FIG. 13.

FIG. 15 is an end view of the proximal end of a compression pad with an extension corresponding to the plunger adapter of FIG. 13.

FIG. 16 is an end view of the distal end of the compression pad of FIG. 13.

FIG. 17 is a perspective view of a piston driven chest compression device with a multi-lobed compression pad engaging a patient with an orientation and defibrillation pad.

FIG. 18 is an end view of the distal end of the compression pad of FIG. 17.

FIG. 19 is an end view of the distal end of an alternate multi-lobed compression pad.

FIG. 20 is a side view of the compression pad of FIG. 19.

FIG. 21 is a perspective view of an alternate compression pads with five appendages.

FIG. 22 is a perspective view of another alternate compression pad with three appendages.

DETAILED DESCRIPTION OF THE INVENTIONS

Figure 6:
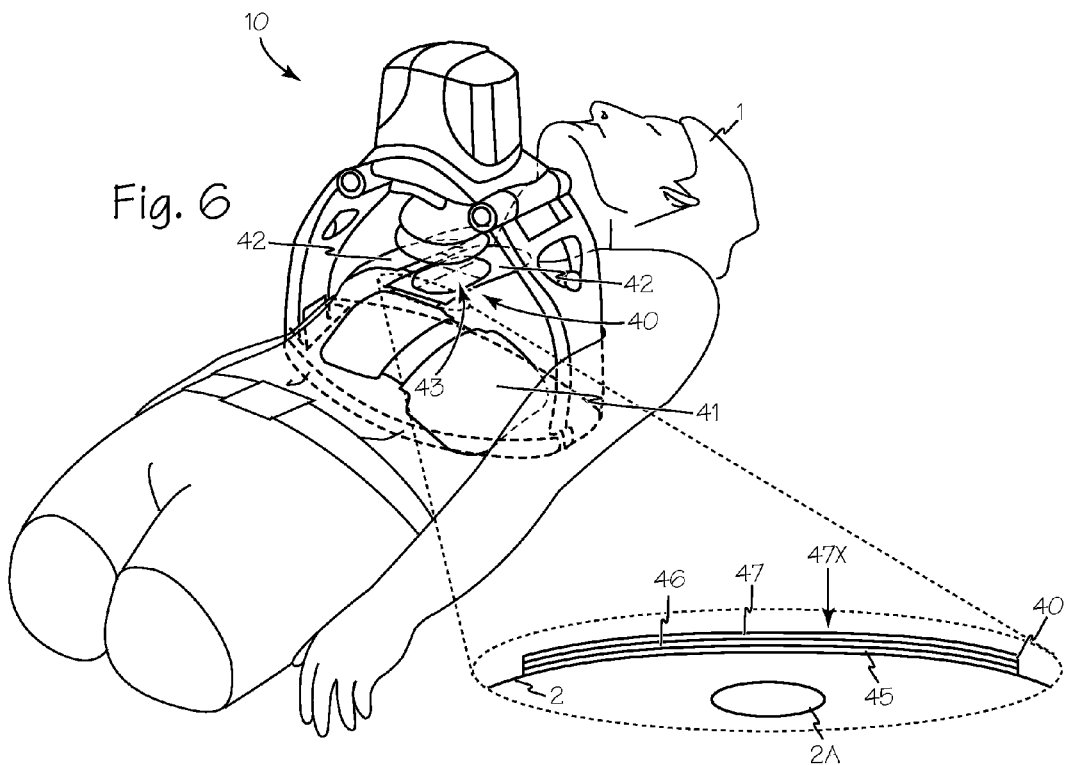
FIG. 6 is a perspective view of a piston driven chest compression device engaging a patient with an orientation and defibrillation pad.

FIGS. 1 and 2 illustrate a piston-based chest compression device installed on a patient. In FIGS. 1 and 2, mechanical chest compression device 10 is oriented to apply compressions to the anterior surface of chest 2 of patient 1. Chest compression device 10 includes support structure 11 which supports and orients chest compression unit 12 apposing sternum 2A. Support structure 11 may be subdivided into legs 11A and 11B and back plate 11C. Chest compression unit 12 includes any suitable drive means such as motor 13 which may be a reversible electromotor, a linear actuator or the like. Plunger 14 has a distal end 14D and a proximal end 14P, and proximal end 14P of the plunger is operably coupled to motor 13. The plunger extends from and withdraws into the housing upon operation of motor 13, and the distal end 14D of plunger impacts the patient's chest. A motor control unit such as controller 15 is operably connected to motor 13 and may include a microprocessor to control the operation of the motor and the plunger. A compression pad 17 (referred to as a compression component by Sibelius) with two or more suction cups 19 applies compression and decompression force to patient 1.

Alternatively, support structure 11 may also have a single leg or post which supports a chest compression unit cantilevered over the patient.

In use, compression pad 17 is removably secured to the patient's chest at force application location 18, which is in a superior position relative to sternal notch 2N as illustrated in FIG. 2. Compression pad 17 may be secured to the patient by suction created by the suction cups 19 formed on distal end 17D. The mechanical chest compression device 10 is oriented around the patient's chest 2 with chest compression unit 12 apposing compression pad 17. Plunger 14 is extended to confirm proper siting of compression pad 17 on the patient and to confirm mating and orientation of plunger adapter 16 with compression pad 17. Upon confirmation of proper alignment and orientation, controller 15 is instructed, through any suitable interface such as interface 12A, to perform cyclic compressions and decompressions for CPR.

Distal end 17D of compression pad 17 may adapt any suitable number and configuration of suction cups as illustrated in FIGS. 3, 4 and 5. Compression pad 20 includes suction cups 22 which are generally the same size and shape and oriented to maintain cup rims 23 in rim plane 24. Rim plane 24 may be curved and may adopt any suitable shape to optimize suction for each of cups 22. Compression pad 27 may include many small suction cups, such as suction cups 28, to control the amount of suction provided by any single suction cup and to minimize the likelihood that loss of suction by any single suction cup will eliminate the decompression force of the chest compression device. Alternate compression pad 30 illustrates a combination of sizes and shapes of suction cups such as round suction cups 31, oval suction cups 32 and small suction cups 33 to provide a controlled and predictable amount of decompression force.

Multiple suction cups and the use of small size suction cups permits the compression pad and the suction cups to conform to complex 3-D surfaces and it also prevents loss of suction by the suction cups at areas of varying or uneven contour on the patient's chest such as occur in the area of the sternal notch.

Figure 7:
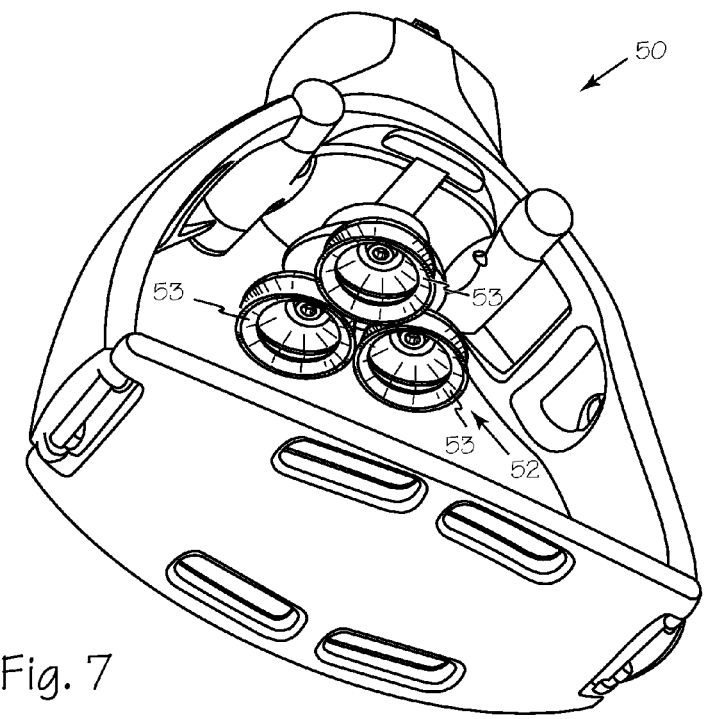
FIG. 7 is a perspective view of a piston driven chest compression device with the compression pad of FIG. 4.

Chest compression and decompression performed by mechanical chest compression device 10 may incorporate compression orientation pad 40. Compression orientation pad 40 may be configured to perform multiple functions and include additional elements such as ECG electrodes 41 as well as defibrillation pads 42 as well as any other suitable components. Compression orientation for chest compression device 10 is provided by compression target 43 which is secured to location 18 by a rescuer before initiation of mechanical chest compression/decompression. Compression orientation pad 40 is secured to the patient's chest using any suitable adhesive such as adhesive 45 forming a layer between pad 40 and chest 2. Compression orientation pad 40 may be formed of one or more layers such as layer 46 which provides structural strength and distributes the compression/decompression forces to the entire area of compression target 43. Sections of pad 40 such as compression target 43 may have additional layers such as top or upper layer 47 which includes a resilient and smooth, surface 47X to optimize the formation of suction in the suction cups of the compression pad used, such as the device illustrated in FIG. 7. Mechanical chest compression device 50 includes compression pad 52 with three round suction cups 53 formed on distal end of the compression pad. Compression orientation pads may include compression targets sized and configured to accommodate various configurations of compression pads such as those illustrated in FIGS. 3, 4, 5, 7 and 8.

Figure 8:
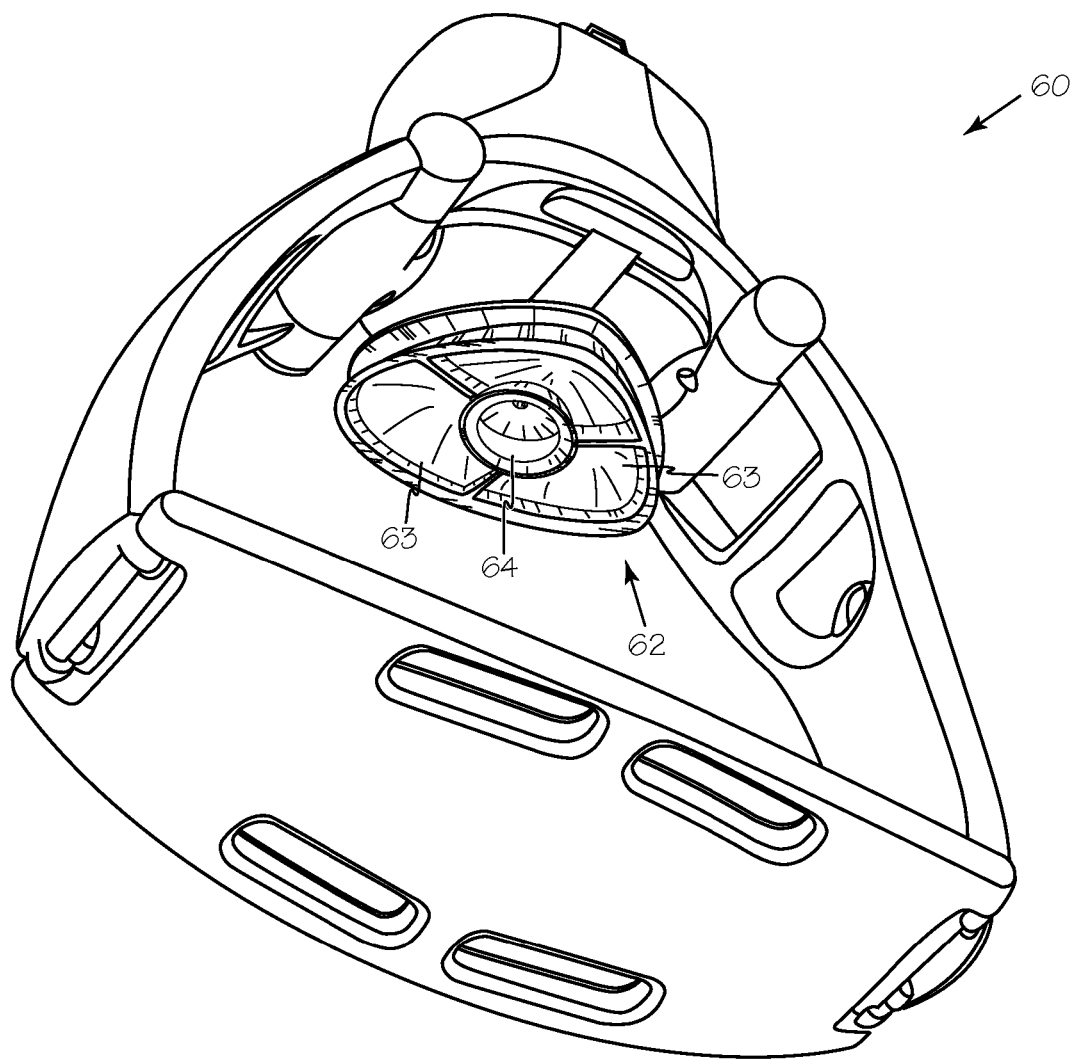
FIG. 8 is a perspective view of a piston driven chest compression device with the proximal end of the compression pad including multiple integrated suction cups.

An alternate configuration of suction cups is illustrated in FIG. 8. Mechanical chest compression device 60 includes compression pad 62 with one or more irregularly shaped suction cups 63 and one or more circular suction cups 64 formed on distal end of the compression pad.

Compression pads with two or more suction cups may be readily combined with cooperating plunger adapters and compression pads as disclosed in our copending U.S. patent application Ser. No. 13/629,434 filed Sep. 27, 2012 which is incorporated herein by reference in its entirety.

To limit the application of excessive decompression force to the chest of a patient undergoing mechanical chest compressions, a separate plunger adapter and compression pad may be used. In FIGS. 9, 10, 11 and 12, plunger adapter 70 has a height or anterior posterior dimension 70D and compression pad 71 has a height or anterior posterior dimension 71D. Proximal end 70P of plunger adapter 70 is removably secured to distal end 72D of plunger 72 using any suitable technique such as mating threads, keyed slots, friction engagement such as socket 70S engaging plunger distal end 72D or any other technique. The height of a plunger adapter and the height of a compression pad may be individually selected to conform to the anterior posterior dimensions of a patient and the length and extension capability of a plunger and compression unit. Compression pad 71 includes extensions such as extension 73 sized to engage a comparably sized socket such as socket 74 in any suitable plunger adapter such as plunger adapter 70. The inner surfaces, surface 74A and surface 74B, of a plunger adapter socket such as socket 74 may include an adhesive or coating such as adhesive layer 75 with a preselected level of adhesion to maintain a limited engagement between a plunger adapter, such as adapter 70, and a compression pad such as compression pad 71, to produce a preselected level of decompression during each retraction of the plunger while performing automated chest compressions to limit or eliminate damage to the patient. Adhesive layer 75 may also be applied to compression pad surfaces 73A and or 73B.

Compression pad 71 is a generally incompressible pad configured to adapt to the shape of the patient's chest. A compression pad such as compression pad 71 may be formed of one or more layers such as first layer 71A and second layer 71B to optimize the application of compressive force to the patient. The proximal or upper end of the compression pad is a generally hard extension or socket such as extension layer 73 for engaging the plunger adapter. The first or central layer, layer 71A may be a flexible and incompressible layer to conform to the shape of the patient's chest. The lower or distal end, second layer 71B, of the compression pad is flexible to adapt to the shape of the patient's chest and may include one or more flexible cups, suction cups 76, for creating one or more areas of vacuum between the compression pad and the patient's chest in suction cup volume 77. When the rim or distal edge 76D of the suction cups are pressed against the surface of the patient's chest, a sticker or other pad and the proximal ends of the suction cups are pressed during chest compression, the volume of the space, suction cup volume 77, within the suction cup and the chest or sticker surface is reduced, which causes the fluid, air, between the cup and the chest to be expelled past the rims of the suction cups. When the chest compression unit ceases to apply compression force and begins the decompression phase of the mechanical CPR process, the material of the compression pad tends to resume its original shape. Because some or all of the air has already been forced out of suction cup volume 77, the pressure in each of the suction cup spaces is lower that atmospheric pressure which enables the compression pad to exert some decompression force on the patient's chest. The pressure developed by a suction cup is a function of the area of the suction cup. Using multiple suction cups on a compression pad enables the pressure of each suction cup is kept low while the combined decompression force of all the suction cups of a compression pad is high enough to provide meaningful chest decompression. Using 10 or more suction cups enables balancing the suction force of multiple small suction cups against the total force for all the suction cups on a compression pad eliminates injury to a patient's chest that may occur with a single large suction cup.

Any suitable smooth sticker sheet or pad such as compression orientation pad 40 or sticker 78 may be removably adhered to a patient's chest to provide smooth surface 78A to optimize the suction between each suction cup and the sticker sheet.

Suitable engagement mechanisms may be included in the plunger and the plunger adapter to provide a preselected level of chest expansion force in addition to chest compression force. A magnet may be provided in the distal end of the plunger and a corresponding magnet or ferrous material may be included in the proximal end of the plunger adapter to provide a preselected retention force between the plunger and the plunger adapter. The retention force is selected to provide some expansion force to the patient's chest between compressions without applying enough expansion force to the patient's chest to tear the patient's skin or underlying tissue. Similarly an electromagnet may be provided in distal end of the plunger to provide an adjustable level of retention force, or to provide timed release of the plunger adapter from the plunger.

As illustrated in FIGS. 13, 14, 15 and 16, plunger adapter 80 includes socket 81 that is sized and dimensioned to engage extension 82 of compression pad 83. Compression pad 83 includes suction cups of varying sizes and configurations such as first suction cups 84, second suction cups 85 and third suction cups 86. The relative sizes, orientation and combinations of sizes and orientation of the suction cups is selected to optimize the compression force, the decompression force provided by the compression pad.

To generate a predetermined decompression force 87 during the retraction of plunger 88, magnets such as adapter magnet 80M and compression magnet 83M may be included in plunger adapter 80 and compression pad 83 to provide the predetermined retention force, such as force of attraction or magnetic force 89, to hold compression pad 83 to plunger adapter 80 until the predetermined decompression force is exceeded. The predetermined level of decompression force is selected to be at a level below which, the chest tissue at force application location 19 will not be damaged before compression pad 83 releases from plunger adapter 80. Any other suitable technique for providing a predetermined level of retention force 89 may be used such as electromagnetic attraction, frictional engagement or others. Any other suitable cooperative configurations of socket and extension may be used.

A compression pad such as compression pad 90 of FIGS. 17 and 18 may adapt any suitable complex shape such as shape 91 with multiple appendages, arms or lobes 92. Distal end 90D of compression pad 90 contain numerous suction cups 94. The use of multiple lobes enables a compression pad with many suction cups to conform to the irregular and complex three-dimensional shapes of patient chest surfaces. Multiple lobes 92 are conformable and inelastic to convey the decompression force between mechanical chest compression device 95 and the anterior surface 2 of the patient's thorax 3, or any sticker or pad adhered to the patient's chest such as compression orientation pad 40. Arms or lobes 92 should be secured to the patient, no lower than the inferior margin of the ribcage and generally constrained to the skin superficial to the anterior surface of the ribcage.

Compression pad 100 of FIGS. 19 and 20 has an irregular shape 101 with five lobes 102. Compression pad 100 includes rigid pad 103 on proximal end 100P to apply compressive force to the patient's chest while flexible and inextensible lobes 102 optimize the application of decompression force to a patient. Distal end 100D includes a multiple suction cups 94 of generally similar size and shape, evenly distributed over the distal end.

As illustrated in FIGS. 21 and 22, compression pads may adopt any suitable shape with two or more lobes. Compression pad 106 of FIG. 21 includes five lobes with lobes 107A and 107B having a different size and shape from lobe 107C, which is again different from lobes 107D and 107E. Depending on the length and flexibility of the lobes, compression pads may include a rigid pad 108 to transfer compression energy from plunger 109 to the patient.

Compression pad 110 of FIG. 22 includes three lobes and each lobe such as lobe 111 may have a different size and shape from lobe 112 which may also be different than lobe 113. The lobes may be rotationally oriented or clocked in any suitable orientation 114 to optimize the compression and decompression forces applied to the patient.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

I claim:

1. A system for compression and decompression of the chest of a patient, the system comprising:
    a mounting structure configured to surround the chest of the patient; and
    a chest compression unit attached to the mounting structure, the chest compression unit comprising:
        a reversible motor;
        a plunger wherein a proximal end of the plunger is operably coupled to the reversible motor;
        a plunger adapter comprising a generally cylindrical adapter wherein a proximal end of the plunger adapter is configured to removably engage a distal end of the plunger;
        a motor control unit operably connected to the reversible motor and the plunger to cyclically provide the compression and the decompression of the chest; and
        a compression pad comprising a frustoconical extension for removably engaging a distal end of the plunger adapter, wherein the distal end of the plunger adapter comprises a frustoconical socket for engaging the compression pad and further wherein the compression pad is configured to conform to a shape of the chest of the patient and comprises two or more suction cups configured to attach the compression pad to the chest of the patient.

2. The system of claim 1 wherein the motor control unit further comprises a microprocessor.

3. The system of claim 1 wherein the two or more suction cups are at least two different sizes.

4. The system of claim 1 wherein the two or more suction cups have at least two different shapes.

5. The system of claim 1 wherein the compression pad further comprises:
    an extension layer at the proximal end of the compression pad configured to removably engage the plunger; and
    a flexible layer attached to the underside of the extension layer and configured to conform to the shape of the chest of the patient; and
    a lower layer attached to the underside of the flexible layer and comprising the two or more suction cups.

6. The system of claim 1 wherein a perimeter encompassing the two or more suction cups defines a shape of a perimeter of the compression pad, the shape of the perimeter of the compression pad comprising one of a rounded triangle, a rounded hexagon, a shape with two or more lobes, or an irregular shape.

7. The system of claim 1 wherein the compression pad is configured to conform to uneven contour areas characteristic of the chest of the patient.

8. The system of claim 1 wherein the compression pad is configured to release from the plunger adapter during the decompression when the decompression force is above a predetermined level of decompression force.

9. The system of claim 8 wherein the predetermined level of decompression force corresponds to a level of decompression force below which the chest tissue of the patient is not damaged before the compression pad releases from the plunger adapter.

10. The system of claim 1 further comprising a compression orientation pad configured to adhere to the chest of the patient and distribute compression and decompression forces from the compression pad.

11. The system of claim 10 wherein the compression orientation pad comprises a compression target section wherein a size and configuration of the compression target section is based on a size and configuration of the compression pad.

12. The system of claim 10 wherein the compression orientation pad comprises defibrillation pads.

* * * * *